United States Patent [19]

Breneman

[11] Patent Number: 5,582,183
[45] Date of Patent: Dec. 10, 1996

[54] APPARATUS FOR ACHILLES TENDON REFLEX TESTING

[76] Inventor: James C. Breneman, 10571 Miller Dr., Galesburg, Mich. 49053

[21] Appl. No.: 508,751

[22] Filed: Jul. 28, 1995

[51] Int. Cl.$^6$ ................................................ A61B 5/103
[52] U.S. Cl. .......................................... 128/774; 128/740
[58] Field of Search ................................... 128/740, 744, 128/739, 782, 774

[56]  References Cited

U.S. PATENT DOCUMENTS

| | | |
|---|---|---|
| 2,685,286 | 8/1954 | Torricelli .................................. 128/740 |
| 2,716,978 | 9/1955 | Torricelli . |
| 2,744,520 | 5/1956 | Torricelli .................................. 128/740 |
| 2,800,895 | 7/1957 | Torricelli . |
| 3,322,115 | 5/1967 | Richards . |
| 3,626,927 | 12/1971 | Breneman ................................. 128/740 |
| 3,734,082 | 5/1973 | Rawson et al. . |
| 3,739,768 | 6/1973 | Rieth ........................................ 128/740 |
| 3,938,503 | 2/1976 | Vis . |

*Primary Examiner*—Max Hindenburg
*Assistant Examiner*—Pamela Wingood
*Attorney, Agent, or Firm*—Price, Heneveld, Cooper, DeWitt & Litton

[57] ABSTRACT

An apparatus for simultaneously causing, measuring, and recording the reflex action of both left and right Achilles tendons of a person to facilitate direct comparison thereof, and to facilitate quicker reflex testing, is provided. The apparatus includes a support structure for positioning a person whose reflexes are to be tested so that both left and right Achilles tendons can be struck simultaneously, a reflex hammer capable of striking both left and right Achilles tendons simultaneously and with substantially identical force, and a device for measuring and recording the reflex movement, of each of the person's feet in response to striking both Achilles tendons.

19 Claims, 3 Drawing Sheets

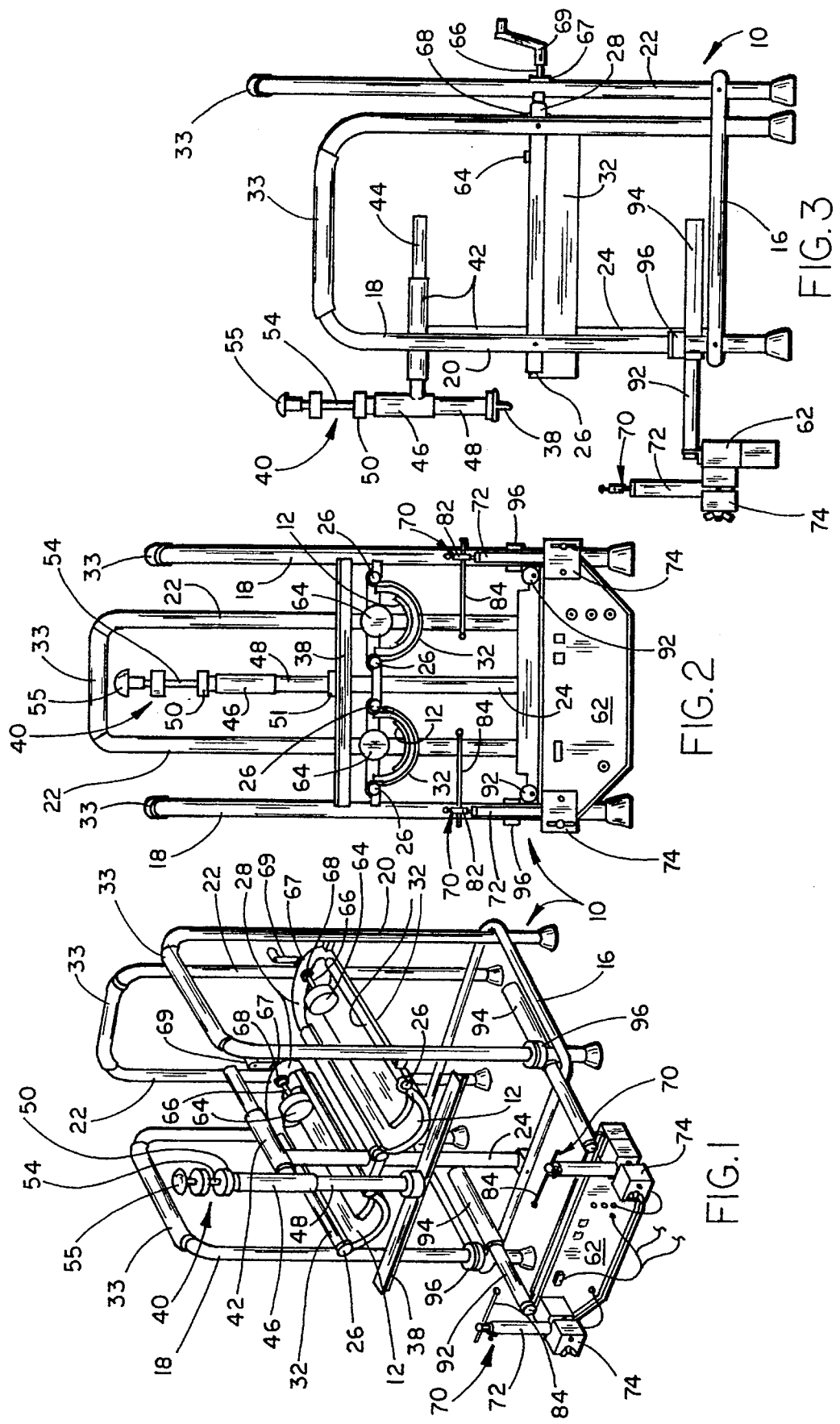

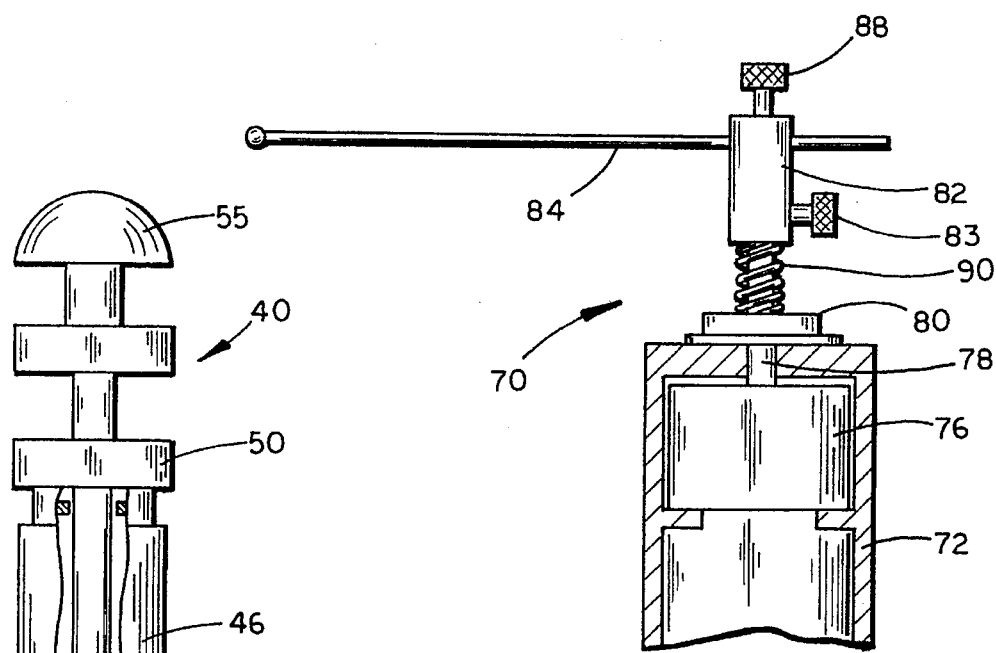
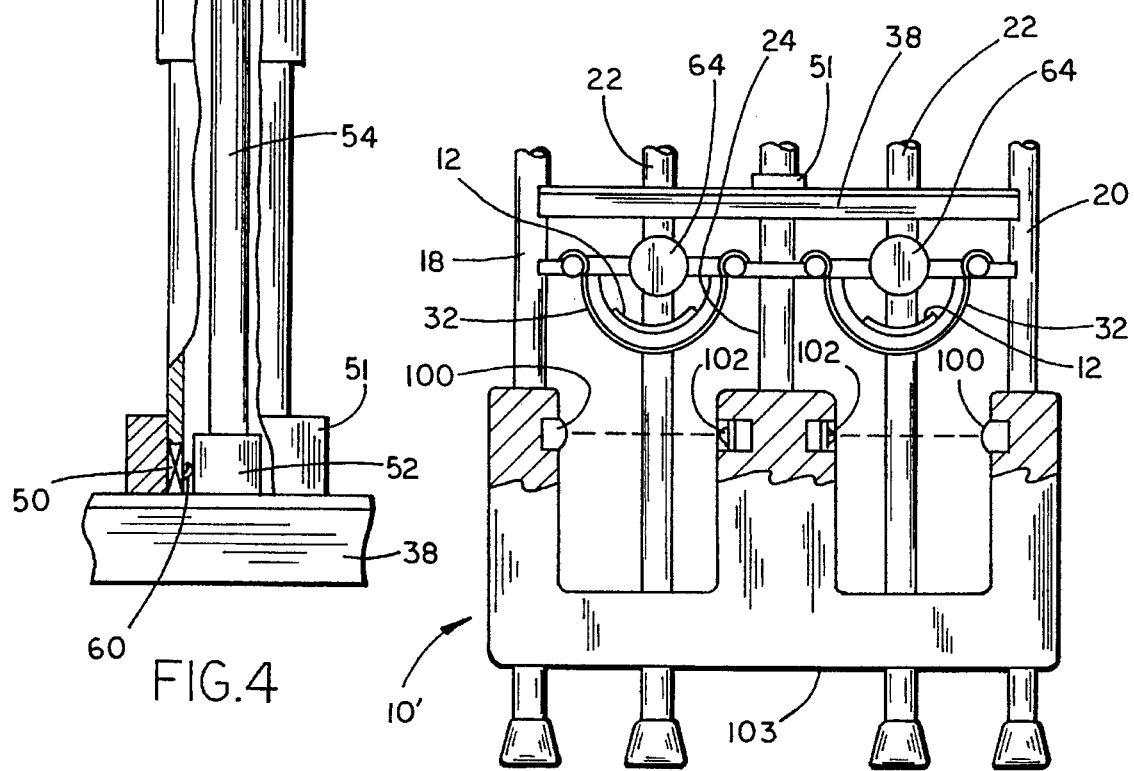

APPARATUS FOR ACHILLES TENDON REFLEX TESTING

BACKGROUND OF THE INVENTION

This invention relates to an apparatus and method for testing reflex action of the Achilles tendons of a human subject to aid in the detection and diagnosis of various disorders and diseases.

It is well established that abnormal reflex action, such as exaggerated, attenuated, or slow reflex actions, can be a symptom indicative of certain diseases, neurological damage, or other physiological disorders. Because of well recognized correlations between abnormal human reflex action and certain medical disorders, and because reflex testing is a relatively inexpensive and nonintrusive procedure for quickly determining whether a patient might be afflicted with such medical disorders, physicians commonly rely on reflex testing as a screening technique during routine physical examination of a patient, with more specific testing generally being recommended to verify or determine the specific disorder afflicting those patients which exhibit abnormal reflexes. Reflex testing is also conveniently used to track the progress of patients which have been diagnosed with, and are being treated for, a particular disease or disorder which affects the patient's reflexes.

In its original and simplest form, reflex testing of the Achilles tendons of a patient was conducted by merely striking the patient's tendon with a reflex hammer and visually observing the reflex action of the patient. A physician could also supplement visual observations with tactile perceptions such as by holding the patient's foot before striking the patient's tendon to sense the force of the reflex actions. Even for highly skilled and experienced physicians, the reliability of detecting abnormal reflexes using manual striking technique and unaided visual and tactile perceptions was not always satisfactory. Moreover, such testing procedures are generally useless for tracking a patient's progress such as to determine whether the patient is responding favorably to a particular treatment. The deficiencies of simple reflex testing procedures including manual striking and sensory observations include the inherent difficulty of striking a patient's Achilles tendon in the same place with the same amount of force for each test, and the difficult of judging whether a particular patient's reflex response deviates significantly from normal based on a comparison of the physician's visual and tactile observations of the patient's reflex response with the physician's memory of similar observations for a normal person.

In attempts to overcome the foregoing problems associated with manual reflex testing and unaided human sensory perception, and thereby improve the reliability and inherent utility of reflex testing, various devices have been developed for striking the Achilles tendon (or other selected portion of a patient's body) with an accurately reproducible, predetermined amount of force, and precisely at the desired position on the tendon, and various other devices have been developed for measuring and recording the reflex action induced by striking the Achilles tendon (or other portion of the patient's body). The problem of precisely striking a desired location on the Achilles tendon with an accurately reproducible amount of force has been solved, for example, by using a reflex hammer having a strike element, which is accurately positioned at the location on the tendon which is to be struck, and an impact member which is subjected to a predetermined, reproducible amount of momentum which is imparted to the strike element upon impacting therewith. For example, a simple, inexpensive reflex hammer which achieves reliable reproducability and utilizes an impact member which is dropped from a predetermined height above a strike element and impacts therewith is described in U.S. Pat. No. 3,626,927, issued to me on Dec. 14, 1971.

Known devices for measuring the reflex action of a patient in response to striking the Achilles tendon include simple mechanical devices, such as those comprising a lever, which is contacted by the patient's foot, and gears which mechanically link the lever with an indicating pointer operable over a dial to provide instantaneous readings of the amount of muscle contraction caused by striking the Achilles tendon. Such measuring devices do not provide a permanent record of the reflex action as a function of time, and are of very limited value for measuring the progress of a patient being treated for a particular disease or disorder which affects the reflexes.

Measuring devices which provide an electrical signal to a recording apparatus to generate a permanent record of reflex action as a function of time have generally been relatively complicated, expensive, and are less accurate than the simple mechanical measuring devices. Such measuring devices having a recordable electrical output include an electromagnetic field generator which is connected with a recording device to record fluctuations in the electromagnetic field caused by movement of a small permanent magnet attached to the patient's foot, which is generally positioned near the center of the electromagnetic field. The electromagnetic field measuring device does not provide an inherently accurate reading of muscle contraction and relaxation as a function of time because the disturbances caused by movement of a magnet through the electromagnetic field cannot be easily or directly correlated with the position of the magnet in the field. The device is also undesirable in view of recent findings which suggest that exposure to electromagnetic fields can be injurious to a person's health.

Another measuring device which is utilized to record reflex responses is a photoelectric detector. The photoelectric device is generally used by positioning the patient's foot so that it partially blocks a light beam directed at the photoelectric detector. The Achilles tendon of the patient is then struck causing the patient's foot to move further into the light beam, generating a change in the photocell voltage which is recorded. As with the electromagnetic field measuring device, the photoelectric device is relatively expensive and may not necessarily provide an accurate record of the position of the foot as a function of time after the Achilles tendon is struck, because the photoelectric detector is only responsive to the amount of light detected, which may not necessarily be directly related to the position of the foot in all cases. For example, errant light sources could interfere with the measurements, and the light beam directed at the photoelectric detector can be fully obscured before peak contraction of the muscle in response to striking the Achilles tendon, thereby making it difficult or impossible to accurately determine the time from peak contraction to when the muscle has relaxed to one-half of its peak contraction, a parameter which is commonly used to characterize reflex action, and used as an aid in diagnosing disease, prescribing treatment, and monitoring a patient's progress.

Another disadvantage with all of the known apparatuses for testing reflex action is that such apparatuses are designed for, and permit only, testing of one of the Achilles tendons at a time. An obvious benefit of testing both Achilles tendons at the same time is that testing can be completed more quickly. A more important, but perhaps less apparent, benefit of testing both tendons simultaneously is that it facilitates direct comparison between the left and right Achilles tendons under substantially identical conditions. Such direct comparisons can be useful for determining the extent of neurological damage caused by traumatic injury such as to only one of a patient's legs, and could serve as a method for early detection of medical disorders which would not ordinarily be expected to affect both Achilles tendons equally, especially during the onset of certain diseases. Accordingly, an apparatus which facilitates direct comparison of reflex action of left and right Achilles tendons under precisely identical conditions can provide early detection of medical disorders, thereby allowing early treatment which will generally minimize a patient's suffering and can, in some cases, minimize or eliminate any permanent damage to the patient. Such direct comparisons can also be beneficial to employers and insurance companies by providing a simple method by which preexisting medical conditions and/or disorders can be detected.

Sequential testing of the left and right Achilles tendons cannot provide direct comparison of the reflex actions thereof, even when performed within a very short interval of time such as within one minute, because a person's reflexes are affected by a wide variety of factors such as heart rate, respiratory rate, blood pressure, body temperature, etc. Moreover, the first test can, by itself, induce physiological and psychological effects which can influence subsequent testing.

In view of the known reflex testing apparatuses, there is a need for an Achilles tendon reflex testing apparatus which is capable of inducing a reflex action in both left and right Achilles tendons simultaneously, and which includes measuring devices for accurately measuring the reflex response of the muscles associated with the left and right Achilles tendons, respectively, and providing a recordable electrical output indicative of the measured reflex responses. Additionally, there is a need for a measuring device, for use with reflex testing apparatuses, which is capable of providing a recordable electrical output signal which is more accurately indicative of the reflexive muscle contraction and relaxation associated with striking an Achilles tendon, and which is relatively simple, reliable, and inexpensive as compared with known measuring devices which provide a recordable electrical signal indicative of a human reflex response.

SUMMARY OF THE INVENTION

The invention provides an apparatus and method for quickly testing the reflex actions of a person in response to being struck upon the Achilles tendons, and which facilitates direct comparison of the left and right Achilles tendons under substantially identical conditions. The invention includes a relatively simple, inexpensive reflex measuring device which provides a recordable electrical output. The measuring device is generally more accurate, more indicative of, and more readily correlatable to, the magnitude of the reflexive movement of a body part in response to the striking of an associated body part, than previous reflex measuring devices providing a recordable electrical output.

In accordance with a preferred aspect of the invention, a reflex testing apparatus for simultaneously testing the left and right Achilles tendons of a persons includes a support structure for positioning the person in a kneeling position so that both left and right Achilles can be struck simultaneously, and a device for measuring the reflex movement caused by striking the Achilles tendons. In accordance with a preferred feature of the invention, the support structure comprises a pair of spaced, parallel, substantially horizontally arranged leg supports having a substantially U-shaped transverse cross section, and a frame onto which the leg supports are mounted. The reflex hammer includes an elongate strike element having portions which are capable of simultaneously contacting both the left and right Achilles tendons, and a hammer element which impacts upon the strike element to transmit momentum through the strike element and to both of the Achilles tendons simultaneously. The hammer element is preferably comprised of a mass which is released and allowed to fall a predetermined distance under the influence of gravity and impact upon the strike element with an accurately reproducible, predetermined amount of force.

Another aspect of the invention pertains to a simple, less expensive mechanoelectrical device for measuring the reflexive movement of a body part in response to striking an associated body part of a human or other mammal. The reflex measuring device includes a lever which is connected to the control shaft of a potentiometer. The lever is positioned so that the magnitude of the lever movement accurately corresponds with the magnitude of the movement of the body part whose movement is being measured. Movement of the lever causes the control shaft on the potentiometer to rotate which in turn changes the electrical resistance of the potentiometer. The change in the electrical resistance of the potentiometer can be easily monitored and recorded such as by measuring and recording the change in electrical current of a circuit including the potentiometer, and/or measuring the voltage drop across the potentiometer. The lever is desirably adjustable connected to a knob attached to the control shaft to allow minor adjustments of the positioning of the lever to accommodate various sized body parts whose movements are to be measured. It is also desirable that the knob be spring biased to urge it back to its normal rest or starting position so that the normal relaxation of a muscle can be accurately monitored as a function of time after it has been contracted by striking an appropriate part of the body associated with the muscle.

In accordance with a further aspect of the invention, a method for simultaneously causing, measuring, and recording reflex actions of the left and right Achilles tendons is provided. The method includes supporting a person's legs in a kneeling position so that both Achilles tendons can be struck simultaneously with an elongate strike element capable of striking both tendons simultaneously, striking the tendons simultaneously, and measuring and recording the reflex actions thereof.

Another further aspect of the invention involves a method of measuring and recording reflex response using an electrocardiograph. The method comprises attaching electrode to a first part of a test object, electronically connecting the electrode to an electrocardiograph, striking an associated part of the test subject's body to elicit a reflex response, and measuring and recording the reflex response on the electrocardiograph.

The apparatus and method of the invention can be advantageously employed during routine physical examinations to provide a quick, easy, convenient, and direct comparison of the reflex responses of the left and right Achilles tendons under substantially identical circumstances, wherein the effects of heart rate, respiratory rate, and various other influences or reflex responses can be eliminated. Such direct comparisons may be extremely useful in the early detection of certain diseases, and could be of great utility to employers and insurance companies interested in quickly screening individuals to detect preexisting diseases or injury. The measuring device is also of great utility in the measurement of a variety of reflex responses, including measurement of Achilles tendon reflex responses, as well as various other reflex responses. More specifically, the potentiometer based, electromechanical measuring device of the invention is relatively inexpensive and generally expected to provide a recordable electrical signal which more accurately reflects the magnitude of the movement being measured than known devices which serve a similar function.

These and other features, advantages and objects of the present invention will be further understood and appreciated by those skilled in the art by reference to the following specification, claims and appended drawings.

BRIEF DESCRIPTION OF THE DRAWINGS

FIG. 1 is a perspective view of an Achilles tendon testing apparatus in accordance with the invention;

FIG. 2 is a front elevational view of the apparatus of FIG. 1;

FIG. 3 is a side elevational view of the apparatus of FIG. 1;

FIG. 4 is an exploded, fragmentary, elevational cross-sectional view showing detail of the reflex hammer used on the apparatus of FIG. 1;

FIG. 5 is an exploded, fragmentary, elevational, partial cross-sectional view showing details of the reflex measuring device used on the apparatus of FIG. 1;

FIG. 6 is a front elevational view of an apparatus which is substantially identical to the apparatus of FIG. 1, except for the use of a photoelectric reflex measuring device;

DETAILED DESCRIPTION OF PREFERRED EMBODIMENT

Figure 7:
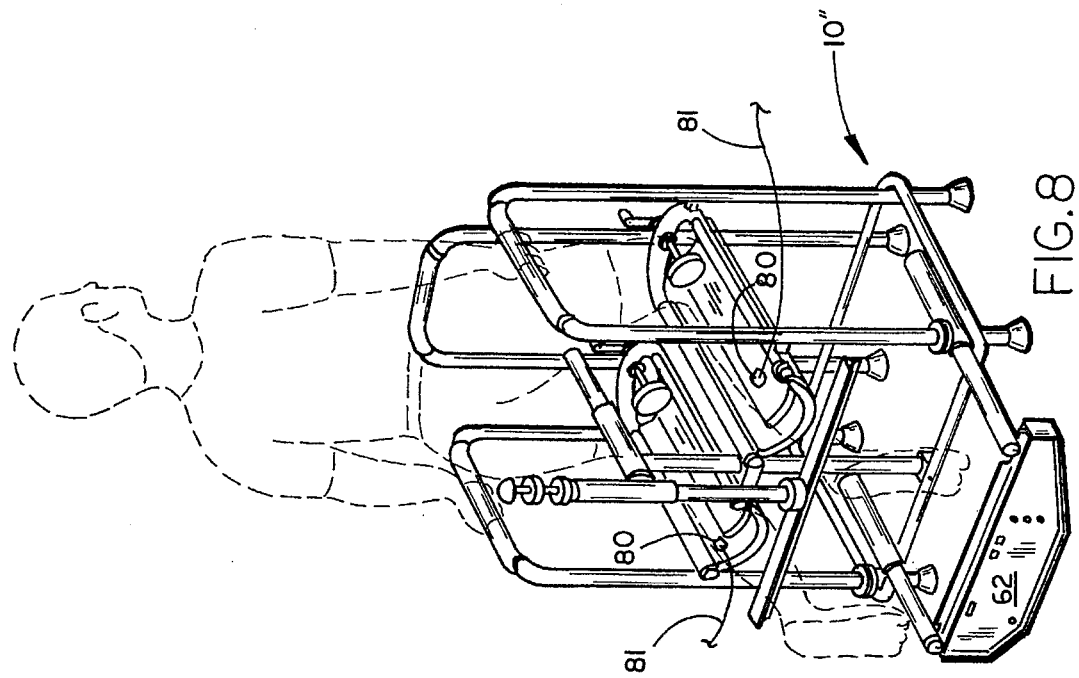
FIG. 7 is a perspective view of the apparatus shown in FIGS. 1–5, and showing a person properly positioned on the apparatus, for testing of the Achilles tendons.
Figure 8:
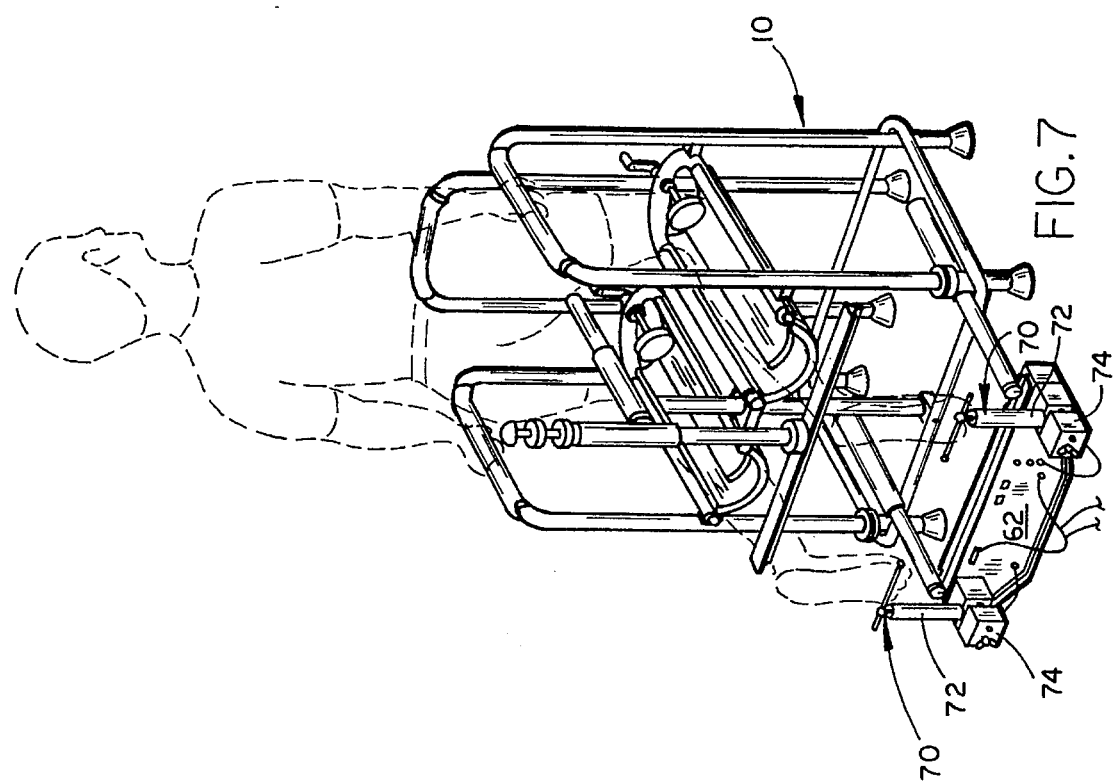
FIG. 8 is a perspective view of an alternative apparatus of the invention, wherein recording and measuring of the reflex response of a text subject is achieved using an electrocardiograph and electrodes suitable attached to the subject's calves.

An apparatus for testing the reflex action of a person's Achilles tendons, which is in accordance with a preferred embodiment of the invention is shown in FIGS. 1–4. With reference to FIG. 1, there is shown a reflex testing apparatus 10 having a support structure including a pair of spaced, parallel, substantially horizontally arranged leg supports 12 for the person's legs. The leg supports 12 are of sufficient length, and are contoured, to comfortably support a person's lower legs from the knee to about the ankles with the feet hanging unsupported over the back end of the leg supports 12. The leg supports 12 which have a substantially U-shaped transverse cross section, are mounted on a frame 14 which places the leg supports at an elevation above a floor which allows the person to easily kneel thereon from a standing position. The frame 14 is comprised of bent aluminum tubing, including a base 16, lateral stanchions 18, 20, 22 and brackets 26, 28. The stanchions 18, 20, 22 are bolted or otherwise fixedly secured to the base 16. The brackets 26, 28 are each bolted or otherwise fixedly secured to one of the lateral stanchions 18 and 20 respectively, to the front stanchion 22, and to the center leg 24.

The leg supports 12 are each comprised of a rigid underlying support member 32 and an overlying cushion 34 (FIGS. 1 and 2). The support member 32 is formed such as by bending or stamping a rigid metal sheet, such as an aluminum sheet, to form an elongate, U-shaped trough or channel having an inverted U-shaped lip portion 36 on each side thereof. The underlying support member 32 is preferably of suitable thickness, such as about 1/16", so that the lip portions 36 can be received onto the tubular brackets 26, 28 and support the weight of a person without any significant strain or deflection of the support member 32 and without any need for bolting the support member 32 to the brackets, thereby eliminating upward projections from the brackets 26, 28 which could poke at a person mounting or dismounting the apparatus or snag a person's clothing. The stanchions 18, 20, 22 are each provided with hand grips 33 which can be used by the person being tested as that person is mounting, dismounting, or kneeling on the apparatus 10. The hand grips can be gripped by the patient to provide additional support, balance, and comfort to the person being tested while that person is kneeling on the apparatus.

An elongate, horizontal strike element 38 and hammer element 40 are supported on the center leg 24. More specifically, a tee 42 secured at the top of the center leg 24 receives a generally horizontal cantilever member 44 having at its rear end a tee 46 in which is received a generally vertical tube 48. The elongate, horizontal strike element 38 is secured at the bottom end of the vertical tube 48. The strike element 38 is of sufficient length to allow simultaneous striking of both left and right Achilles tendons of a person being tested. As illustrated, the strike element 38 has a continuous T-shaped transverse cross section. However, element 38 need not have a continuous cross section to achieve the objectives of the invention, it being possible to strike both tendons simultaneously with any element having a pair of strike surfaces or edges, each of which strikes a respective one of the tendons. The vertical tube 48, which is vertically movable within tee 46 includes a stop 50 attached at its top end which rests against the top edge of tee 46 to support the tube 48, hammer 40 and strike element 38 when the apparatus is not in use. Referring to FIG. 4, the hammer 40 includes an internal weight 52 secured to a plunger rod 54. The rod 54 has a handle 55 attached to its top end and a stop 56 which is fixed to a portion of the rod within the tube 48. The top 56 engages an internal ring 58 fixed at the top end of tube 48 when the rod is lifted upwardly to limit and indicate the extent of upward travel of the hammer rod 54. The hammer 40 generally comprising weight 52, rod 54, handle 55, and stop 56, is falls through tube 48 which acts as a guideway directing the momentum of the hammer against the center (and center of mass) of the strike element to strike each tendon (left and right) with substantially identical force. At the bottom interior of tube 48 is an electrical switch 58 having a ball shaped button 60 which projects slightly into the interior of the hollow tube 48 and is engaged by weight 52 when the rod 54 is at its lowest position within tube 48 with stop 50 resting against the top edge of tee 46. The switch 58 closes an electrical circuit when the rod 54 is at its lowest position within tube 48 to provide a signal to a microprocessor located within an electrical housing 62. The signal can be used to start a recorder or to indicate on a recording when the Achilles tendons were struck to induce a reflex action.

The strike element 38 and hammer 40 are mounted onto the center leg 24 in a manner which permits complete adjustability of the positioning of the strike element on a person's Achilles tendons to accommodate people of various proportions. In particular, tee 42 is rotatably attached to the top of leg 24 to allow lateral adjustment of the positioning of strike element 38, horizontal cantilever member 44 is axially slidable within tee 42 to allow adjustment of the strike element 38 along the longitudinal direction of the apparatus 10, and tube 48 is axially slidable within tee 46 to allow vertical adjustment of the position of strike element 38. As an aid to maintain proper positioning of the person kneeling on the leg supports 12 of apparatus 10, each leg support is provided with a knee stop 64 which is supported on a rod 66 passing through one of the brackets 26 or 28 and through one of the legs of stanchion 22. Rods 66 are threaded and carry internally threaded lock nuts 68 which allow the stops 64 to be approximately positioned along the length of the leg supports 12 to accommodate people of varying proportions so that the knees of the particular person being tested abut the stops 64 with the person's ankles generally overlapping the rear edge of the leg supports with the person's feet hanging freely from the leg supports.

A pair of reflex measuring devices 70 are mounted on the electrical housing 62 to measure foot movement of a person being tested and provide a recordable electrical signal indicative of the person's foot movements in response to being struck on the Achilles tendons. Each reflex measuring device includes a hollow cylindrical pedestal 72 secured to the electrical housing by a clamp 74. As shown in FIG. 5, positioned within the pedestal, near the top end thereof, is a variably adjustable resistor or potentiometer 76, similar to the volume control on a radio or television receiver, having a control shaft 78 which can be rotated to vary the electrical resistance of the potentiometer. Rotatable shaft 78 is vertically arranged and projects upwardly through an opening in a cap 80 at the top of the pedestal 72. A knob 82 is fixed to the top of shaft 78. A small diameter rod or lever 84 which passes through a horizontal base in knob 82 acts as a detector element which is contacted by the foot of the person being tested. The lever 84 is slidable within the horizontal bore when set screw 88 is loosened, and lockable at a desired position within the bore when the set screw is tightened. The knob 82, having attached lever 84, is spring biased by means of a spiral torsional spring 90 disposed over shaft 78 with its spiral axis generally coinciding with the axis of shaft 78. One end of the spring 90 is attached to the knob 82, and the other end of the spring is attached to a portion of the reflex measuring device which remains stationary during reflex testing, such as the cap 80. The spring 90 urges the knob 82 back to its normal resting or starting position so that the foot position of the person being tested can be tracked and recorded from the relaxed starting position before the Achilles tendons are struck, through the fully extended position of the foot corresponding with the peak contraction of the muscles associated with the Achilles tendons, and back to the relaxed position. Unless the knob 82 is urged back to the starting position, it is not possible to determine the time from peak construction to half relaxation, which time is generally regarded as an important characteristic of the reflex response.

The electrical housing 62, on which the measuring devices 70 are mounted, is secured to the frame 14 by a pair of cantilever support beams 92, which are slidingly received within hollow support tubes 94, each of which is attached to a corresponding rear leg of one of the stanchions 18, 20 by a clamp 96. Clamps 96 are slidable on the rear legs of stanchions 18, 20 and lockable at a desired position thereon to allow upward and downward movement of the measuring devices 70 as needed to accommodate people of various proportions. Measuring devices 70 can also be positioned as desired along the longitudinal direction of the apparatus as needed to accommodate people of various proportions by sliding beams 92 forward or backward within tubes 94. Additional adjustability of the positioning of measuring devices 70 is provided by clamps 74, each of which can be loosened by rotation of wing nut 98. After clamp 74 is loosened, pedestal 72 can be raised or lowered, rotated and retightened in a desired position. Clamps 74 are also preferably pivotally mounted to the electrical housing 62 to allow rotation of the measuring devices 70 on an axis parallel with the longitudinal direction of the apparatus 10. Further adjustability of the apparatus is provided by loosening set screws 88 and sliding rods 84 within a born through each of knobs 82. While the degree of adjustability of the positioning of the strike element 38 and the measuring devices 70 generally exceeds that necessary to test the vast majority of people, it is nevertheless available for exceptional circumstances, such as to accommodate unusually tall or unusually short people.

The electrical housing 62 will generally contain means for supplying appropriate electrical current to the switch 58 and to the potentiometers 76, means for measuring the change in resistance in potentiometer 76 caused by rotation of knobs 82, and a microprocessor for receiving the potentiometer readings and signal from switch 58, and means for providing an electrical signal to a recording device to record the switch signal and the potentiometer readings.

The apparatus 10 is used by having a person kneel on the leg supports 12 with their feet dangling freely over the back end thereof. The strike dement 38 is then properly positioned on the Achilles tendons (both left and right) at the locations which are to be struck. Next, measuring devices 70 are properly positioned adjacent to the bottoms of the person's feet so that when a reflex action is induced by striking the Achilles tendons the measuring devices will track the movement of the feet and provide an electrical signal indicative of the reflex response. After checking that power is being supplied to the switch 58 and potentiometer 76, and that the output of electrical signal from the potentiometers is properly connected to a microprocessor or recording device, the handle 55 is raised a predetermined distance above strike element 38 or, alternatively, a predetermined distance above an anvil contained within tube 48 or disposed between tube 48 and strike element 38. The handle is then released causing the mass of the hammer 40 to accelerate under the influence of gravity through a predetermined change in elevation whereupon the hammer abruptly impacts on the strike element 38 or a part, such as an anvil, attached thereto, instantaneously transferring a predetermined and accurately reproducible amount of force or momentum to the strike dement, which force or momentum is transmitted to both the left and right Achilles tendons. Because a strike element having rigidly connected strike surfaces or edges for each of the Achilles tendons is used, and because the impact between the strike element and the hammer element occurs substantially at the center of the strike element, each of the Achilles tendons is simultaneously struck with substantially identical force, thereby facilitating direct comparison of the reflex responses of the left and right Achilles tendons. Other types of hammers can also be used for impacting the strike element. For example, mass can be accelerated toward the strike dement using a spring, solenoid or the like. At the moment the Achilles tendons are struck or immediately therebefore the hammer activates a switch which provides an electrical signal which can be used to trigger a recording device or indicate the start of the test, so that the duration of time between striking of the Achilles tendons and peak contraction of the muscles associated with the Achilles tendons, or other reflex characteristics, can be determined. As the feet of the person being tested move rearwardly, levers or detector elements 84 are pushed backwards causing knobs 92 to rotate, which in turn changes the resistances of potentiometers 76. The change in resistances of the potentiometers 76 can be easily detected and recorded using various well-known, commercially available devices.

In order to facilitate mounting of the apparatus 10, by a person who is to be tested, the hammer 40 and strike element 38 are preferably removable such as by completely sliding cantilever member 44 out of tee 46 and setting the hammer and strike element aside temporarily to facilitate unobstructed access to the leg supports 12. The hammer 40 and strike element 38 can be easily replaced as a unit, after the person to be tested is properly positioned kneeling on the leg supports, by reinserting member 44 into tee 46. Also, to facilitate mounting of the apparatus 10 by a person, the clamps 74 and attached measuring devices 70 can be temporarily rotated outwardly out of the way. After testing is completed, the hammer 40 and strike dement 38 can be removed again, and clamps 74 and measuring devices 70 can again be rotated out of the way to allow the person tested to easily dismount the apparatus 10.

In accordance with another aspect of the invention, the apparatus 10' can be used with photoelectric measuring devices 100, as shown in FIG. 6. The apparatus is generally similar to that of the previously described embodiment shown in FIGS. 1–5, except that the electromechanical measuring devices 70 have been eliminated and replaced with a pair of photoelectric detectors 100. Also provided are a pair of appropriate light sources 102 for directing a beam of light toward the photoelectric detectors. The photodetectors 100 and corresponding light sources 102 are moved inwardly/outwardly and upwardly/downwardly together in a manner substantially identical with the manner in which electrical housing 62 and measuring devices 70 are positioned on the apparatus 10 shown in FIGS. 1–5. The photodetectors 100 and light sources 102 are positioned so that the light beams directed toward the photodetectors 100 will be obscured by movement of the feet of the person being tested, after being struck on the Achilles tendons. The amount of light which is blocked is related to the extent to which the foot is moved backward away from its rest position. As is well known, a change in the amount of light reaching the photodetectors 100 will cause a change in the photocell voltage which can be measured and recorded to provide a permanent record indicative of the person's reflex response to being struck on the Achilles tendons.

The above description is considered that of the preferred embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

The embodiments of the invention in which an exclusive property or privilege is claimed are defined as follows:

1. An apparatus for simultaneously testing the reflex action of both left and right Achilles tendons of a person, comprising:

a support structure for positioning a person whose reflexes are to be tested so that both left and right Achilles tendons can be struck simultaneously;

a reflex hammer including a strike element having portions which simultaneously contact left and right Achilles tendons of the person whose reflexes are to be tested, and a hammer element which impacts upon said strike element to transmit momentum through said strike element to both left and right Achilles tendons simultaneously; and a device for measuring the amount of reflex movement caused by simultaneously striking the Achilles tendons whereby direct comparisons of the left and right tendons can be made under identical psychological and physiological conditions.

2. The apparatus of claim 1, wherein said support structure includes a pair of spaced, parallel, substantial horizontally arranged leg supports having a substantially U-shaped transverse cross section, and a frame onto which said leg supports are mounted;

said leg supports being of sufficient length and being contoured to support both lower legs of a person from the knee to about the ankles.

3. The apparatus of claim 2, wherein said leg supports each comprise a rigid underlying support member and an overlying cushion.

4. The apparatus of claim 1, wherein said hammer element comprises a mass which is released to accelerate under the influence of gravity through a predetermined change in elevation and impact upon said strike element to transfer a predetermined amount of momentum thereto, which is transmitted to both the left and right Achilles tendons simultaneously.

5. The apparatus of claim 4, wherein said apparatus further comprises a guideway which directs the momentum of the hammer against the center of mass of the strike element when said hammer is released to accelerate under the influence of gravity so that the strike element will impart substantially identical forces to each of the tendons.

6. The apparatus of claim 5, wherein said guideway is a tube having a stop which limits and indicates the extent of upward travel of said hammer in said tube, said strike element and said stop generally defining said predetermined change in elevation through which said hammer is released to accelerate under the influence of gravity.

7. The apparatus of claim 1, wherein said device for measuring the amount of reflex movement caused by striking the Achilles tendons comprises a lever operatively connected to the control shaft of a potentiometer, said lever being positionable adjacent the bottom of the feet of the person to be tested, so that movement of said feet caused by a reflex response upon striking the Achilles tendons causes movement of said lever thereby changing the electrical resistance of said potentiometer.

8. The apparatus of claim 7, wherein said control shaft is arranged vertically and has a knob on its upper end, and said lever passes through a horizontal base in said knob.

9. The apparatus of claim 8, wherein said lever is slidable within said base, and lockable at a desired position within said base.

10. The apparatus of claim 8, wherein said knob is spring biased to urge the knob back to a normal rest position after being moved by a reflex action induced by striking the Achilles tendons.

11. The apparatus of claim 10, wherein said spring is a spiral torsional spring disposed over said control shaft, one end of said spring being attached to the knob, and the other end being attached to a portion of the measuring device which remains stationary during reflex testing.

12. The apparatus of claim 1, wherein said frame includes an upright member and a horizontal, cantilever support member which is rotatably secured to said upright member for angular movement about the vertical axis of said upright member and slidingly supported on said upright member for longitudinal movement perpendicular to the vertical axis of said upright member, and wherein said reflex hammer and said strike element are supported on said cantilever member.

13. The apparatus of claim 12, wherein said hammer and strike element are slidingly supported for vertical movement with respect to said cantilever member.

14. The apparatus of claim 13, wherein said measuring device is supported from said frame for vertical movement and for horizontal movement along the longitudinal direction of said apparatus.

15. The apparatus of claim 1, wherein said device for measuring the amount of reflex movement caused by striking the Achilles tendons comprises a light source and a photoelectric detector responsive to said light source.

16. A method for directly comparing the reflex response of left and right Achilles tendons under substantially identical conditions, comprising:
supporting both of the legs of a person in a kneeling position so that both of the Achilles tendons can be struck simultaneously;
striking both left and right Achilles tendons simultaneously with an elongate strike element having portions which contact and strike both tendons; and
measuring and recording the reflex action of the left and right Achilles tendons.

17. The method of claim 16, wherein the step of supporting both legs of a person in a kneeling position involves positioning the lower portion of the persons legs on a pair of spaced, parallel, substantially horizontally arranged leg supports having a substantially U-shaped transverse cross section.

18. The method of claim 17, wherein the step of striking both left and right Achilles tendons simultaneously is achieved by releasing a weight and allowing it to accelerate under the influence of gravity and impact upon said strike element.

19. The method of claim 18, wherein said step of measuring and recording is achieved by positioning a lever operatively connected to the control shaft of a potentiometer adjacent to the bottom of the feet of the person being tested, so that the movement of said feet causes movement of said lever thereby changing the electrical resistance of said potentiometer, and recording the change in the electrical resistance of said potentiometer in response to striking said tendons.

* * * * *

UNITED STATES PATENT AND TRADEMARK OFFICE
CERTIFICATE OF CORRECTION

PATENT NO. : 5,582,183
DATED : Dec. 10, 1996
INVENTOR(S) : James C. Breneman

It is certified that error appears in the above-indentified patent and that said Letters Patent is hereby corrected as shown below:

Column 6, Lines 43 thru 48;

Delete "and a stop . . . hammer rod 54

Column 6, Line 48;

After "40" insert –,–.

Column 6, Line 48,

After "rod 54," insert –and–.

Column 6, Line 49;

After "handle 55" delete –, and stop 56, is–.

Column 6, Lines 57 and 58;

After "tube 48" delete –with stop 50 resting against the top edge of tee 46–.

UNITED STATES PATENT AND TRADEMARK OFFICE
CERTIFICATE OF CORRECTION

PATENT NO. : 5,582,183
DATED : Dec. 10, 1996
INVENTOR(S) : James C. Breneman

It is certified that error appears in the above-indentified patent and that said Letters Patent is hereby corrected as shown below:

Column 8, Line 13;

"born" should be --bore--.

Col. 8, lines 30 and 51;

"dement" should be --element--.

Column 8, Line 62;

"dement" should be --element--.

Column 9, Line 21;

"dement" should be --element--.

Signed and Sealed this

Ninth Day of September, 1997

Attest:

BRUCE LEHMAN

Attesting Officer

Commissioner of Patents and Trademarks